(12) United States Patent
Sano et al.

(10) Patent No.: US 6,495,132 B2
(45) Date of Patent: Dec. 17, 2002

(54) METHOD FOR PRODUCING POLYPEPTIDES

(75) Inventors: Ken-ichi Sano, Kamigori-machi (JP); Kayo Maeda, Shingu-machi (JP); Yuichiro Maeda, Shingu-machi (JP)

(73) Assignee: Riken, Wako (JP)

( * ) Notice: Subject to any disclaimer, the term of this patent is extended or adjusted under 35 U.S.C. 154(b) by 0 days.

(21) Appl. No.: 09/859,773

(22) Filed: May 17, 2001

(65) Prior Publication Data

US 2002/0127710 A1 Sep. 12, 2002

(30) Foreign Application Priority Data

May 17, 2000 (JP) ......................................... 2000-144518

(51) Int. Cl.[7] ...................... A61K 48/00; C12N 15/866; C12N 15/63; C12N 5/10
(52) U.S. Cl. .................... 424/93.2; 424/93.1; 424/93.6; 435/455; 435/456; 435/325; 435/320.1; 435/69.1; 435/348; 536/23.1; 536/23.5; 536/24.1
(58) Field of Search ................................ 435/455, 456, 435/325, 320.1, 69.1, 348; 424/93.1, 93.2, 93.6; 536/23.1, 23.5, 24.1

(56) References Cited

PUBLICATIONS

Donald L. Mykles et al, Cloning of tropomyosins from lobster (Homarus americanus) striated muscles: fast and slow isoforms may be generated from the same transcript, Journal of Muscle Research and Cell Motility 19, 105–115, (1998).*

* cited by examiner

*Primary Examiner*—David Guzo
(74) *Attorney, Agent, or Firm*—Heslin Rothenberg Farley & Mesiti P.C.

(57) ABSTRACT

There is provided a method for producing a polypeptide using a recombinant baculovirus according to the present invention, wherein said recombinant baculovirus is constructed by ligating the untranslated region of 21 base pairs as set forth in SEQ ID NO:1 upstream of the lobster tropomyosin coding sequence wherein the level of expression of the polypeptide in the baculovirus is remarkably enhanced. There is also provided the polynucleotide sequence of 21 base pairs as set forth in SEQ ID NO:1 and the transfer vector containing the sequence, the recombinant baculovirus genome containing the sequence and the recombinant baculovirus containing the recombinant baculovirus genome to use in the above method.

37 Claims, 3 Drawing Sheets

SEQUENCE LISTING

<160> NUMBER OF SEQ ID NOS: 11

<210> SEQ ID NO 1
<211> LENGTH: 21
<212> TYPE: DNA
<213> ORGANISM: Homarus americanus

<400> SEQUENCE: 1
aactcctaaa aaaccgccac c                                              21

<210> SEQ ID NO 2
<211> LENGTH: 29
<212> TYPE: DNA
<213> ORGANISM: Artificial Sequence
<220> FEATURE:
<223> OTHER INFORMATION: PCR primer

<400> SEQUENCE: 2
ggtctagaaa ctcctaaaaa accgccacc                                      29

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
ttggatccga gagtgtttag tagccagac                                      29

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
ctgttggtaa agccaccatg g                                              21

<210> SEQ ID NO 5
<211> LENGTH: 26
<212> TYPE: DNA
<213> ORGANISM: Artificial Sequence
<220> FEATURE:
<223> OTHER INFORMATION: PCR primer

<400> SEQUENCE: 5
ggatccttac acggcgatct ttccgc                                         26

<210> SEQ ID NO 6
<211> LENGTH: 46
<212> TYPE: DNA
<213> ORGANISM: Artificial Sequence
<220> FEATURE:
<223> OTHER INFORMATION: portion of multicloning site of pVL1392

<400> SEQUENCE: 6
agatctgcag cggccgctcc agaattctag aaggtacccg ggatcc                   46

<210> SEQ ID NO 7
<211> LENGTH: 46
<212> TYPE: DNA
<213> ORGANISM: Artificial Sequence -continued

```
<220> FEATURE:
<223> OTHER INFORMATION: complementary strand of sequence id. no. 6

<400> SEQUENCE: 7
tctagacgtc gccggcgagg tcttaagatc ttccatgggc cctagg                46

<210> SEQ ID NO 8
<211> LENGTH: 35
<212> TYPE: DNA
<213> ORGANISM: Artificial Sequence
<220> FEATURE:
<223> OTHER INFORMATION: sequence representing XbaI recognition site
      of pVL1392 vector, sequence id. no. 1 and first 8 nucleotides
      of coding sequence of lobster Tm cDNA

<400> SEQUENCE: 8
tctagaaact cctaaaaaac cgccaccatg gacgc                             35

<210> SEQ ID NO 9
<211> LENGTH: 49
<212> TYPE: DNA
<213> ORGANISM: Artificial Sequence
<220> FEATURE:
<223> OTHER INFORMATION: portion of multicloning site of pAcC4

<400> SEQUENCE: 9
acctataacc atggcggccc gggtacctgc agatctagaa ttcggatcc              49

<210> SEQ ID NO 10
<211> LENGTH: 49
<212> TYPE: DNA
<213> ORGANISM: Artificial Sequence
<220> FEATURE:
<223> OTHER INFORMATION: complementary strand of sequence id. no. 6

<400> SEQUENCE: 10
tggatattgg taccgccggg cccatggacg tctagatctt aagcctagg              49

<210> SEQ ID NO 11
<211> LENGTH: 26
<212> TYPE: DNA
<213> ORGANISM: Artificial Sequence
<220> FEATURE:
<223> OTHER INFORMATION: sequence representing NcoI recognition site of
      pAcC4 vector and first 24 nucleotides of coding sequence of rabbit
      skeletal muscle .-Tm cDNA

<400> SEQUENCE: 11
ccatggacgc catcaagaag aagatg                                       26
```

METHOD FOR PRODUCING POLYPEPTIDES

CROSS-REFERENCE TO RELATED APPLICATIONS

This application claims priority under 35 U.S.C. §119 of Japanese application number P200-144518 filed May 17, 2000, the contents of which are hereby incorporated by reference in their entirety.

FIELD OF THE INVENTION

The present invention relates to a method for producing polypeptides. More particularly, the present invention relates to the method for producing polypeptides in insects and/or cultured insect cells by recombination technology to enhance the efficiency of production of the polypeptides.

BACKGROUND OF THE INVENTION

Many methods for producing a polypeptide or a protein have been developed up to now. For example, taking a protein, a biological component as an example, it is possible to prepare the protein sample directly from living body, but it has generally some problems in large scale production, high cost as well as heterogeneity due to the presence of isoforms in the case of enzymes. Recently the genetic engineering method is most frequently used. In that case, the method using E. coli is mostly employed. E. coli is easy to handle and the expression in the E. coli-based system is most rapid, but it has also some problems. Because E. coli is a prokaryote, there frequently occurred the problems such that water insoluble protein is formed due to unsuitable folding when the protein is an exogenous protein from a eukaryote and that modifications of the protein that are important for its function do not take place after translation in E. coli cells. In that case, the method using baculovirus to express such a protein in a cultured insect cell is usually employed for avoiding the above problems. However, in this system, small amounts of the expressed protein provide a perplexing problem.

SUMMARY OF THE INVENTION

Accordingly, the object of the present invention is to provide a method to solve the above problems that amounts of the expressed protein are small when the protein is expressed in an insect or a cultured insect cell by using baculovirus.

The present inventors carried out the expression of tropomyosin protein from several kinds of organisms and surprisingly found that only the amount of tropomyosin from lobster is remarkable and more than 30-fold high as compared with, for example, that from rabbit. Based on that finding, the present inventors studied more and more and found the untranslated polynucleotide sequence from lobster has a function enhancing the expression of proteins. The present invention is based on these findings and accomplished by further studies.

Accordingly in the first aspect of the present invention, there is provided a base sequence of SEQ ID NO:1 which is an untranslated leader sequence from lobster having a function enhancing the expression of a coding sequence located downstream thereof. All the base sequences obtained by deletion, substitution, insertion and/or addition of one or more nucleotides in the base sequence set force in SEQ ID NO:1 are also included in the present invention as far as these base sequences have a function enhancing the expression of a coding sequence located downstream thereof.

In the second aspect of the present invention, there is provided a transfer vector obtained by inserting the base sequence of SEQ ID NO:1 or the base sequence obtained by deletion, substitution, insertion and/or addition of one or more nucleotides in the base sequence set force in SEQ ID NO:1 having a function enhancing the expression of a coding sequence located downstream thereof and a DNA sequence coding a polypeptide of interest ligated downstream of said base sequence into the position downstream of the promoter sequence from baculovirus. Such promoter sequences from baculovirus include polyhedrin gene sequence. This promoter is used for integration of the transfer vector into baculovirus genome. Such vectors containing the promoter from baculovirus include, for example pVL1392 vector. When this vector is used, it is preferable to insert the sequence of SEQ ID NO:1 and the like of the present invention and a DNA sequence coding a polypeptide of interest ligated downstream thereof in the multicloning site of the vector.

In the third aspect of the present invention, there is provided a recombinant baculovirus genome capable of expressing a polypeptide of interest, which is constructed by integrating the base sequence relating to the expression of the polypeptide of interest from the transfer vector of the present invention into a baculovirus genome by in vivo homologous recombination. The homologous recombination may occur in an insect or a cultured insect cell or in a yeast cell or an E. coli cell. The insect mentioned above is preferably silkworm and the cultured insect cell is preferably a Sf9 cell, Sf21 cell or High five (trademark) cell (Invitrogen). The base sequence relating to the expression of polypeptide of interest may be inserted into baculovirus genome by means of trans element from transposon in E. coli cells. In this case, a commercially available kit may be used.

In the fourth aspect of the present invention, there is provided a recombinant baculovirus having the recombinant baculovirus genome of the present invention. The recombinant baculovirus can be obtained by transfecting the recombinant baculovirus genome prepared in the third aspect of the present invention into an insect or a cultured insect cell capable of being host for baculovirus.

In the fifth aspect of the present invention, there is provided a method for producing a polypeptide of interest comprising a step of infecting an insect or cultured insect cell with the recombinant baculovirus of the present invention to express the polypeptide of interest in the cell and a step of collecting the expressed polypeptide.

The polypeptide of interest in the above second to fifth aspects of the present invention includes interferon β, interferon γ, interleukin-1 α, interleukin-1 β, interleukin-2, interleukin-3, interleukin-4, interleukin-5, interleukin-6, cow-somatotropin, erythropoietin, granulocyte colony-stimulating factor, granulocyte macrophage colony-stimulating factor, macrophage colony-stimulating factor, blood clotting factor VII, blood clotting factor VIII, blood clotting factor IX, blood clotting factor XIII, skeletal growth factor, colony-stimulating factor, epithelial growth factor, growth hormone releasing factor, fibroblast growth factor, tissue plasminogen activator, transforming growth factor, thrombopoietin, luciferase and the like as well as tropomyosin, but is not limited thereto. Among them, glycoprotein such as interferon β, interferon γ, interleukin-1 α, interleukin-1 β, interleukin-5, erythropoietin, granulocyte colony-stimulating factor, granulocyte macrophage colony-stimulating factor, macrophage colony-stimulating factor, blood clotting factor VII, blood clotting factor VIII, blood clotting factor IX, blood clotting factor XIII, tissue plasminogen activator, thrombopoietin and the like are preferable as the protein of interest for the present invention.

All patent applications, patents and literature references cited herein are hereby incorporated by reference in their entirety.

DETAILED DESCRIPTION OF THE INVENTION

The sequence of the present invention having a function enhancing the expression of polypeptide is the untranslated leader sequence from lobster, namely, aactcctaaa aaaccgccac c (SEQ ID NO:1).

The base sequences obtained by deletion, substitution, insertion and/or addition of one or more nucleotides in the base sequence set forth in SEQ ID NO:1. having the function enhancing the expression of the coding sequence located downstream thereof are also included in the present invention. These sequences may be obtained by chemical synthesis or derived from tropomyosin cDNA from lobster according to the conventional methods.

Figure 1:
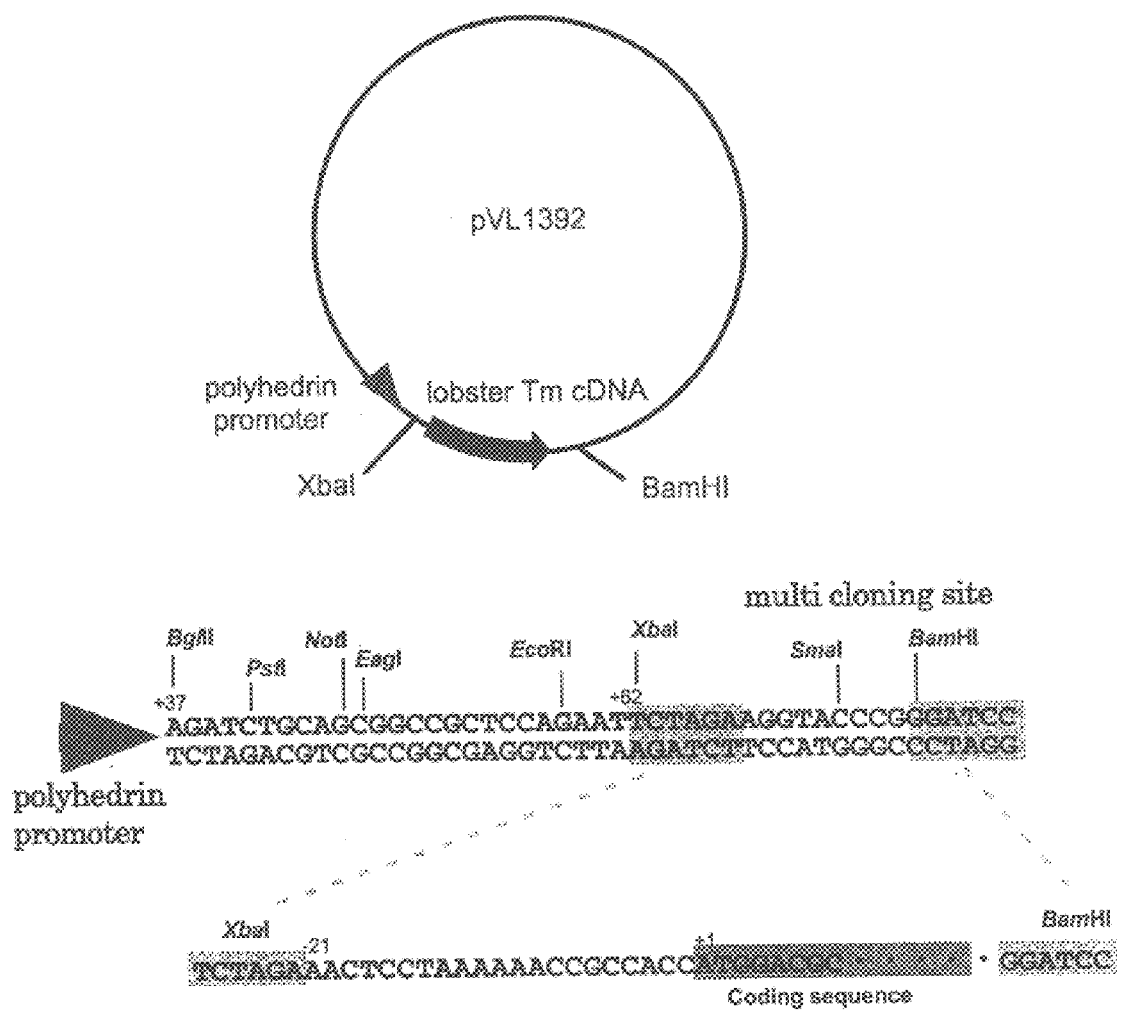
FIG. 1 shows schematically the transfer vector constructed by inserting tropomyosin cDNA from lobster between XbaI site and BamHI site in the multicloning site of the vector pVL1392. It is shown that the untranslated region of 21 base pairs from tropomyosin cDNA is located upstream of the tropomsyoin coding sequence and downstream of XbaI site. The initiation codon of polyhedrin promoter is broken.

The transfer vector to express the polypeptides of the present invention may be obtained as follows. Namely, the transfer vector may be prepared by preparing a base sequence comprising the base sequence of SEQ ID NO:1 of the present invention and a DNA sequence coding a polypeptide of interest ligated downstream thereof wherein said base sequence has the restriction sites corresponding to the following multicloning site according to the usual method and inserting said base sequence into the multicloning site, for example, between XbaI site and BamHI site of pVL1392 vector appended to Baculogold Transfection Kit (PharMingen). Alternatively, the transfer vector to express the polypeptide of interest may be generally constructed by digesting the transfer vector to express tropomyosin constructed as described above with NcoI-BamHI to remove the coding region of tropomyosin from lobster and inserting a cDNA coding the polypeptide of interest thereto. An outline of an example of thus obtained transfer vector to express the polypeptide is schematically shown in FIG. 1. In the Figure, 21 base pairs between XbaI site and the coding sequence are the untranslated leader sequence from lobster set forth in SEQ ID NO:1 of the present invention. This sequence, as a whole or a part thereof and a sequence having this sequence or a part thereof can be used for the present invention as far as the sequence retains the function enhancing the expression, namely, the function remarkably enhancing the expression of polypeptide coded by the coding sequence ligated downstream of the sequence.

The polypeptide coded by the coding sequence ligated downstream of the sequence of the present invention in the transfer vector to express the polypeptide of the present invention includes, for example tropomyosin, luciferase, interferon β, interferon γ, interleukin-1 α, interleukin-1 β, interleukin-2, interleukin-3, interleukin-4, interleukin-5, interleukin-6, cow-somatotropin, erythropoietin, granulocyte colony-stimulating factor, granulocyte macrophage colony-stimulating factor, macrophage colony-stimulating factor, blood clotting factor VII, blood clotting factor VIII, blood clotting factor IX, blood clotting factor XIII, skeletal growth factor, colony-stimulating factor, epithelial growth factor, growth hormone releasing factor, fibroblast growth factor, tissue plasminogen activator, transforming growth factor, thrombopoietin and the like, but is not limited thereto. Among them, glycoprotein such as interferon β, interferon γ, interleukin-1 α, interleukin-1 β, interleukin-5, erythropoietin, granulocyte colony-stimulating factor, granulocyte macrophage colony-stimulating factor, macrophage colony-stimulating factor, blood clotting factor VII, blood clotting factor VIII, blood clotting factor IX, blood clotting factor XIII, tissue plasminogen activator, thrombopoietin and the like are preferable as the polypeptide of interest for the present invention.

A recombinant baculovirus of the present invention is constructed as follows. The recombinant baculovirus may be constructed by integrating a sequence relating to the expression of polypeptide from the above transfer vector to express polypeptides into a baculovirus genome by in vivo homologous recombination of the above transfer vector to express polypeptides with the baculovirus genome in a living cell and selecting the recombinant baculovirus of interest. The living cell for carrying out in vivo homologous recombination is preferably an insect or a cultured insect cell capable of being host for baculovirus, but a method employing a yeast or E. coli cell has also been developed. The insect is preferably silkworm.

When the homologous recombination is carried out in a cultured insect cell, for example, a method comprising using an Sf9 cell, Sf21 cell or High five™ (Invitrogen) cell as the cultured insect cell, carrying out the transfection of baculovirus with the transfer vector using Baculogold Transfection Kit (PharMingen) according to the protocol appended thereto and selecting the recombinant baculovirus according to the plaque assay method may be used for the present invention,.

When the homologous recombination is carried out in a yeast cell, the recombinant baculovirus may be isolated according to the description of D. M. Glover and B. D. Hames, DNA Cloning 2 Expression Systems, Second Ed., A Practical Approach.

Also, the recombinant baculovirus may be prepared via the recombinant baculovirus genome in an E. coli cell using, for example Gibco BRL Bac-to-Bac Baculovirus Expression System (Life Tech). In brief, the recombinant baculovirus of interest may be obtained by (1) inserting a gene encoding protein to be expressed into a particular recombinant donor plasmid in flame, (2) transforming an *E. coli* DH10Bac cell using obtained vector, (3) screening it with an antibiotic or a β-galactosidase enzyme to obtain the recombinant, (4) collecting the recombinant Bacmid DNA from the obtained recombinant and confirming its identity by PCR and (5) transfecting an insect cell with the obtained Bacmid DNA and culturing it for 5 to 7 days.

Usually, thus obtained recombinant baculovirus is preferably amplified in need, added fetal bovine serum to be about 4% of final concentration if fetal bovine serum contained in the medium is low and preserved at 4° C. to be used for the expression of polypeptide. Also, the preservation of the recombinant baculovirus for long term may preferably be carried out in subdivision and at −80° C.

The polypeptide of interest is usually produced using the recombinant baculovirus of the present invention as follows. First, an insect cell, for example an Sf9 cell is cultured. When the cell concentration is reached at a suitable level, the above recombinant baculovirus is added to the cell at an enough multiplicity of infection. Further the cell is cultured for suitable period and centrifuged for collection of the cell. Then, the cell is lysed in a hypotonic cell-lysing solution and the protein of interest can be isolated and purified from the supernatant obtained by centrifugation of the lysate according to a conventional method. Also when a membrane protein is expressed, the cell is lysed in a solution containing a surfactant.

From the results of the experiments using tropomyosin as a polypeptide of interest, it is clear that the sequence (SEQ ID NO:1) of the present invention is effective for the expression of a coding sequence downstream thereof. In brief, the tropomyosin cDNA from rabbit skeletal muscle was firstly inserted into pAcC4 transfer vector according to the usual method (Kluwe L. et al., Journal of Muscle Research and Cell Motility 16, 103–110 (1995)) and the transfer vector was then integrated into baculovirus. When the baculovirus was expressed in an Sf9 cell, the amount of the expressed tropomyosin was about 20 to 30 mg/3L. On the other hand, when tropomyosin was expressed by the recombinant baculovirus having the sequence (SEQ ID NO:1) of the present invention upstream of the lobster tropomyosin coding sequence, the amount of the expressed tropomyosin was about 600 to 1200 mg/3L. This amount is about 30 to 40 times greater than those of the expressed rabbit tropomyosin by the expression system not containing the sequence of the present invention. Further, when the tropomyosin cDNA from rabbit skeletal muscle was inserted into the transfer vector to express tropomyosin containing the sequence (SEQ ID NO:1) of the present invention and expressed by the recombinant baculovirus constructed by homologous recombination containing the sequence of the present invention upstream of rabbit tropomyosin cDNA, it was observed that the rabbit tropomyosin was expressed in amount as much as that of lobster tropomyosin containing the sequence of the present invention, differing from the expression by the recombinant baculovirus not containing the sequence of the present invention.

These observations shows that the untranslated region of 21 base pairs of the present invention has the effect enhancing the expression of the coding sequence ligated downstream thereof up to 30 to 40 times.

EXAMPLES

Basic genetic engineering was according to Sambrook, J., Fritsch, E. F. and Maniatis, T., Molecular Cloning: A Laboratory Manual, 2nd Ed., (1989), Cold Spring Harbor Laboratory, Cold Spring Harbor N.Y.

Basic method of culturing insect cell, having baculovirus is used according to he following manuals.

O'Reilly, D. R., Miller, L. K. and Luckow, V.P.A. (1992), Baculovirus Expression Vectors: A Laboratory Manual, W. H. Freeman and Co., New York. Summers, M. D. and Smith, G. E. (1987) A Manual of Methods for Baculovirus Vectors and Insect Cell Culture Procedures, Texas Agricultural Experiment Station Bulletin No. 1555.

Example 1

Construction of a Transfer Vector to Express Tropomyosin from Lobster Muscle

A 0.5 ml tube was charged with 0.2 µg of tropomyosin cDNA from lobster muscle, each 100 pico mole of the following two synthetic DNAs, namely, ggtctagaaa ctcctaaaaa accgccacc (SEQ ID NO:2) and ttggatccga gagtgtttag tagccagac (SEQ ID NO:3), 1 µl of ExTaq polymerase (Takara), 10 µl of 10xbuffer appended to the polymerase, and 8 µl of dNTP mixture and the final volume of the solution in the tube was adjusted to 100 µl with distilled water. Then the tube was loaded on a PCR apparatus Zymoreactor II (Atto Corporation) to carry out PCR by reaction program comprising 93° C. for 5 minutes, 25 cycles comprising each cycle of 93° C. for 1 minute, 55° C. for 1 minute and 72° C. for 1 minute, and 72° C. for 10 minutes. The PCR product contained restriction enzyme XbaI site, the untranslated region of 21 base pairs upstream of translation initiation codon and the entire translated region of tropomyosin from lobster muscle and restriction enzyme BamHI site. Both the PCR product and the transfer vector, pVL1392 were digested with XbaI/BamHI (Takara) and then subjected to a 0.8% TAE-agar gel electrophoresis. After the electrophoresis, the gel was stained with ethidium bromide and its DNA bands were detected on a transiluminater. The bands of tropomyosin cDNA and pVL1392 fragments were cut by a cutter to extract DNAs by Gene Clean II Kit (BIO101). These DNAs were mixed, followed by addition of T4 DNA ligase (Takara) and the mixture was incubated at 16° C. for overnight. After the incubation, the resulting base sequence was transformed to *E. coli* cells, which were grown on an LB agar medium containing ampicillin to form colonies. The formed colonies were picked up with a toothpick and cultured on a Circle grow medium (BIO101) to be well grown. The transfer vector was prepared by using Plasmid Maxi Prep Kit (Qiagen). In the transfer vector (FIG. 1), the initiation codon of original polyhedrin downstream of polyhedrin promoter had been destroyed and the tropomyosin gene from lobster containing the untranslated region of 21 base pairs is inserted between XbaI site and BamHI site downstream of the destroyed initiation codon.

Comparative Example 1

Construction of the Transfer Vector to Express Rabbit Muscle Tropomyosin

Figure 2:
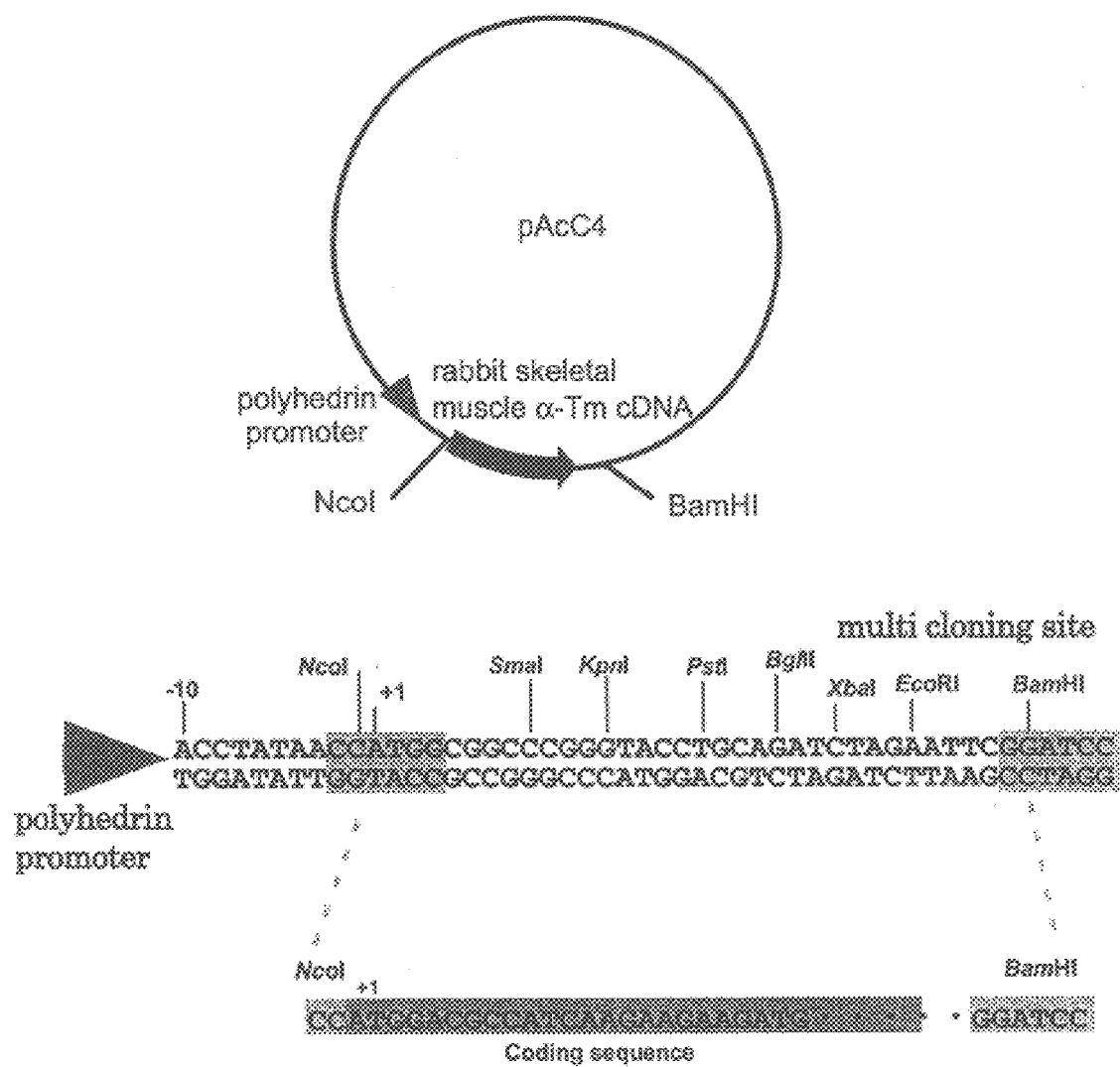
FIG. 2 shows schematically the transfer vector constructed by inserting α-tropomyosin cDNA from rabbit skeletal muscle between NcoI site and BamHI site of the vector pAcC4. In this vector, the tropomyoisn coding sequence is ligated immediately downstream of NcoI site.

Both the tropomyosin cDNA from rabbit muscle and the transfer vector, pAcC4 were digested with restriction enzymes NcoI/BamHI (Takara), followed by a 0.8% TAE-agar gel electrophoresis. After the electrophoresis, the DNA fragments were stained with ethidium bromide and the DNA bands were detected on a transilluminator. The bands of tropomyosin cDNA and pAcC4 fragments were cut by a cutter to extract DNA by Gene Clean II Kit (BIO101). These DNAs were mixed, and to the mixture added T4 DNA ligase (Takara) and the appended buffer thereto and the mixture was incubated at 16° C. for overnight. After the incubation, the resulting base sequence was transformed to E. coli cells, which were grown on a LB agar medium containing ampicillin to form colonies. The formed colonies were picked up with a toothpick and cultured on a Circle grow medium (BIO101) to be well grown. The transfer vector was prepared by using Plasmid Maxi Prep Kit (Qiagen). In the transfer vector (shown in FIG. 2), the tropomyosin gene from rabbit was inserted downstream of the initiation codon of original polyhedrin downstream of polyhedrin promoter.

Example 2

Figure 3:
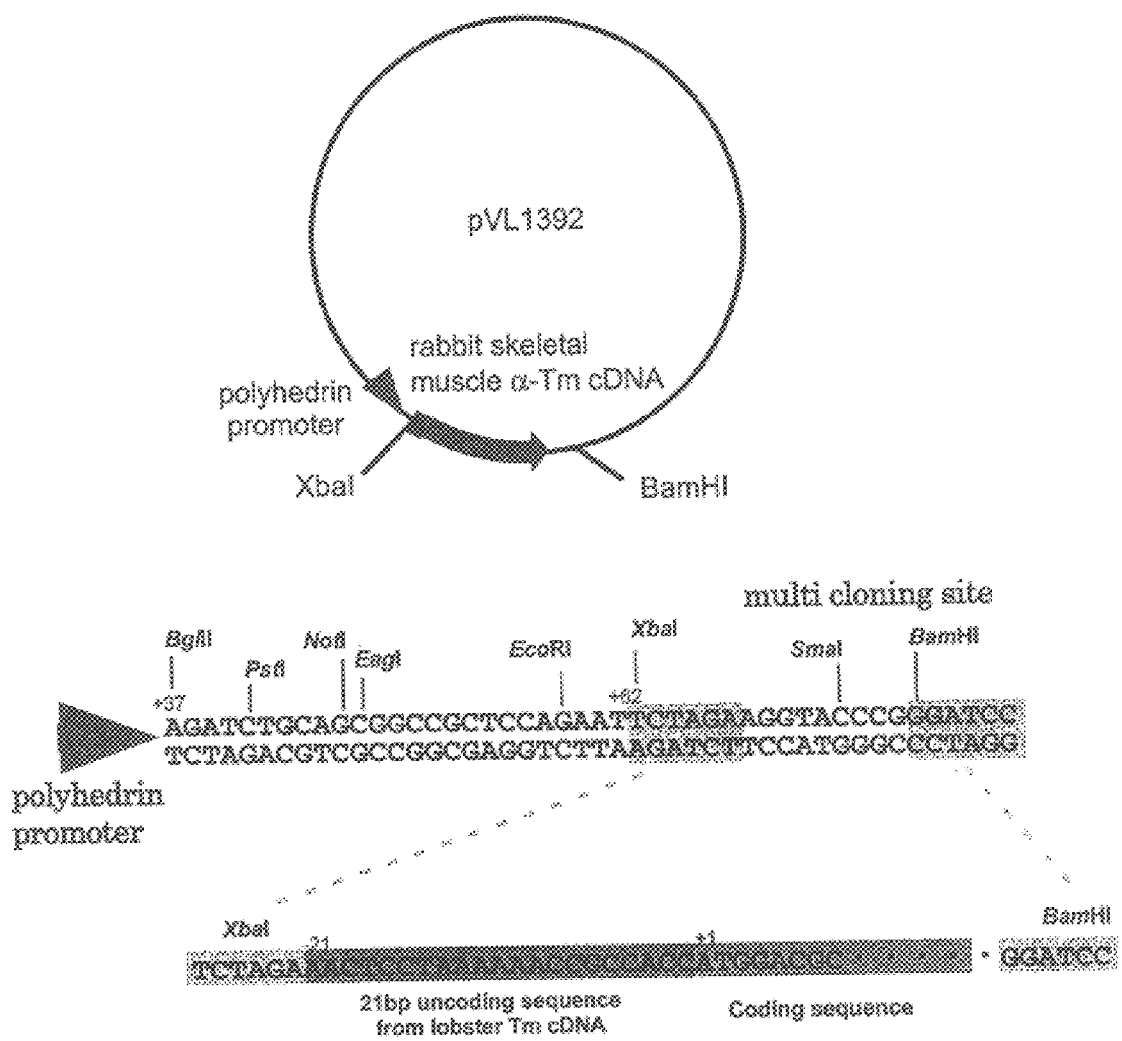
FIG. 3 shows schematically the transfer vector constructed by inserting α-tropomyosin cDNA from rabbit skeletal muscle between XbaI site and BamHI site in the multicloning site of the vector pVL1392. It is shown that the untranslated region of 21 base pairs from lobster tropomyosin cDNA is located upstream of the rabbit tropomyosin coding sequence and downstream of XbaI site.

Construction of a Transfer Vector to Express Rabbit Muscle Tropomyosin Containing the Untranslated Region of 21 Base Pairs from Lobster Tropomyosin This construction was carried out in a similar manner as in the above construction of the transfer vector to express tropomyosin from rabbit muscle. The different point is that the cDNA from rabbit muscle was inserted into not the transfer vector pAcC4 but the transfer vector to express tropomyosin from lobster muscle digested with NcoI/BamHI to remove the coding region of lobster tropomyosin. In the transfer vector (shown in FIG. 3), the initiation codon of original polyhedrin downstream of polyhedrin promoter was destroyed and the tropomyosin gene from rabbit was inserted downstream of the untranslated region of 21 base pairs from lobster tropomyosin gene adjacent to XbaI site further downstream.

Example 3

Preparation of the Recombinant Baculovirus and Amplification Thereof

Using the transfer vectors constructed in Example 1, Comparative Example 1 and Example 2, Sf9 cells were transfected according to the protocol appended to Baculogold Transfection Kit (PharMingen). After that, the recombinant viruses were screened by the following plaque assay method.
<Plaque Assay Method>
This Method Comprising the Following Steps:
(1) Diluting Sf9 cells cultured in the TNM-FH medium containing 10% FBS (inactivated bovine fetal serum, Sigma) to $5 \times 10^5$ cells/ml;
(2) Sowing 4 ml of the cells prepared in step (1) on a 6-cm plate for cell culture (No. 3002) (Falcon);
(3) Standing the plate at 27° C. for 30 minutes;
(4) Sucking up the medium and in place of that adding 2 ml of the virus solution diluted with the TNM-FH medium containing 10% FBS to a suitable concentration,
(5) Standing the plate at 27° C. for 1 hour;
(6) Sucking up the virus solution in the plate, adding 4 ml of 50° C. TNM-FH medium containing 1.5% low melting point agar and 10% FBS and standing the plate at room temperature until the agar solidifies;
(7) Cultivating the plate at standing state at 27° C. for 4 days, then overlaying 2 ml of 50° C. TNM-FH medium containing 0.01% neutral red, 0.75% low melting point agar and 10% FBS and standing the plate at room temperature until the agar solidifies;
(8) Standing the plate at 27° C. for 4 hours; and
(9) Selecting single plaque which was discolored by a Pasteur pipet.
After the screening according to the above method, the selected viruses were amplified 3 times as follows.

<Amplification of the Virus I>
First Amplification Comprises the Following Steps:
(1) Carrying out the plaque assay again for the single plaque;
(2) Diluting Sf9 cells cultured in the TNM-FH medium containing 10% FBS to $5 \times 10^4$ cells/ml with the same medium and putting 2.5 ml of the Sf9 cells into a 6-well plate (No. 3046, Falcon);
(3) Putting the 4 plaques obtained from step (1) in each well;
(4) Culturing the well at standing state at 27° C. for 5 days; and
(5) Transferring the culture into a 15 ml centrifuge tube (No. 2097, Falcon), centrifuging at 1,200×G for 10 minutes and collecting the supernatant containing the viruses.
<Amplification of the Virus II >
Second Amplification Comprises the Following Steps:
(1) Diluting Sf9 cells cultured in the TNM-FH medium containing 10% FBS to $4 \times 10^5$ cells/ml with the same medium and putting 5 ml each of the Sf9 cells into two 25 cm$^2$ flasks (No. 3055, Corster);
(2) Adding 20 µl of the amplified virus obtained from <Amplification of the virus I> to each flask from step (1);
(3) Culturing the cells in each flask at standing state at 27° C. for 7 to 10 days; and
(4) Mixing the cultures of the two flasks, transferring the mixture into a 15 ml centrifuge tube (Falcon), centrifuging the mixture at 1,200×G for 10 minutes and collecting the supernatant containing the viruses.
<Amplification of the Virus III>
Third Amplification Comprises the Following Steps:
(1) Culturing Sf9 cells with stirring at 27° C. in a modified Sf900II medium (90% Sf900II medium (Gibco), 9% Grace's insect medium supplemented (Gibco), 1% FBS) containing 850 to 900 ml of 0.2% Pluronic F68 (Gibco) in a 3L spinner flask (BELLCO) until the cell concentration reaches 1.8 to $2.0 \times 10^6$ cells/ml wherein the stirring is carried out at about 90 to 100 rpm by a magnetic stirrer (WAKENYAKU);
(2) Adding 5 ml each of the virus solution obtained from <Amplification of the virus II >to each flask;
(3) Culturing the mixture of virus and cells in the flasks at standing state at 27° C. for 7 to 10 days;
(4) Mixing the cultures, transferring the culture into a 225 ml centrifuge tube (No. 2075, Falcon), centrifuging at 1,200×G for 10 minutes and collecting the supernatant containing the virus;
(5) Adding FBS to the virus solution to final concentration of 4% and preserving it at 4° C.; and
(6) Simultaneously, checking the titer of virus according to the plaque assay method mentioned above.

Example 4

Expression of the Polypeptide by Baculovirus-Sf9 Cell System

This Example was performed using Cell Master Controller (WAKENYAKU). Sf9 cells were cultured in 3L of modified Sf9OOII medium containing 0.2% Pluronic F68 (Gibco) at 27° C. with stirring in a 3L spinner flask (BELLCO). The concentration of oxygen was controlled between 60 to 70% of the saturated oxygen concentration of water. The stirring was carried out at 70 to 80 rpm by using a magnetic stirrer (BELLCO). When the cell concentration reached 1.8 to $2.0 \times 10^6$ cells/ml, the virus solution prepared in <Amplification of the virus III> was added to the culture with about 2.0 of the multiplicity of infection. Further the cells were cultured for additional 48 to 52 hours with stirring. After that, the cells were collected by centrifugation. Simultaneously, 10 ml of the culture was transferred into a 15 ml centrifuge tube (Falcon) to check the expression and the culture was centrifuged at 1,500×G for 10 minutes to collect the cells.

<Check of the Expression>

500 μl of a hypotonic cell lysis solution (20 mM Tris-HCl, pH8.0, 1 mM EDTA, 5 mM DTT) was added to the collected cells to check the expression above described. By pipetting, the cells were lysed, transferred to a 1.5 ml tube and centrifuged at 15,000 rpm for 15 minutes on a centrifuge (MX-160, Tomy). The supernatant was collected and incubated at 95° C. for 10 minutes. After that, the sample was gradually cooled at room temperature and centrifuged at 15,000 rpm for 5 minutes on a centrifuge (Tomy). 10 μl of the supernatant was subjected to an SDS-PAGE. The concentration of acrylamide was 15%. After the electrophoresis, the gel was stained by Coomassie Brilliant Blue and the amount of the expression of the band corresponding to tropomyosin was determined by densitometry using a Gel-Doc 2000 (BioRad).

Partial Purification of the Expressed Tropomyosin

Sf9 cells expressing tropomyosin by the above method were treated according to the following methods to partially purify the expressed tropomyosin, determine the concentration of protein and analyze the amount of expression.

<Determination of Rabbit Skeletal Muscle Tropomyosin>

The Procedures Comprises the Following Steps:
(1) Adding 100 ml of a hypotonic cell lysis solution (20 mM Tris-HCl, pH8.0, 0.1 mM EDTA, 5 mM DTT) to the collected cells, lysing the cells by pipetting and centrifuging at 38,000×G for 30 minutes to collect the supernatant;
(2) Adding ammonium sulfate to the supernatant at the final concentration of 35%, stirring it for more than 30 minutes and centrifuging at 38,000×G for 30 minutes to collect the supernatant;
(3) Adding ammonium sulfate to the supernatant at the final concentration of 70%, stirring it for more than 30 minutes and centrifuging at 38,000×G for 30 minutes to collect the precipitates and discard the supernatant;
(4) Dissolving the precipitates in 100 to 150 ml of a solution containing 10 mM Tris-HCl, pH8.0, 0.1 mM EDTA, 5 mM DTT and dialyzing it against the same solution;
(5) Transferring the dialysate to a glass beaker and putting the beaker in a hot bath at 90° C., cooling the sample slowly to room temperature 10 minutes after the time when the sample temperature reached 85° C. as measured by a thermometer in the sample and centrifuging the sample at 38,000×G for 30 minutes to collect the supernatant after the sample being cooled down to the room temperature;
(6) Adjusting the pH of the supernatant to 4.5 by adding HCl to the supernatant obtained in step (5) while monitoring the pH by a pH meter, centrifuging the solution at 38,000×G for 30 minutes and discarding the supernatant;
(7) Dissolving the precipitates obtained from step (6) in about 50 ml of a solution containing 10 mM Tris-HCl, pH 8.0, 0.5 mM DTT and dialyzing it against the same solution; and
(8) Determining the concentration of total protein of the dialysate by the micro-bullet method and determining the amount of total protein, carrying out SDS-PAGE of the dialysate (see <check of the expression>), determining the ratio of tropomyosin with respect to the total protein by densitometry as above described and estimating the amount of tropomyosin.

<Purification of Lobster Tropomyosin>

The above-described method (<Determination of rabbit skeletal muscle tropomyosin>) was slightly modified.

The Modified Points Were as Follows:
(a) Lysing the cells in 500 ml of a hypotonic cell lysis solution in (1);
(b) Adding NaCl to the lysate with the final concentration of 0.1 M, between (1) and (2);
(c) Using 200 to 250 ml of the solution to dissolve the precipitates in (4); and
(d) Using about 150 ml of the solution to dissolve the precipitates in (7).

Example 5

Expression of Lobster Tropomyosin

As shown in Comparative Example 2, it has been found that the expression level of tropomyosin of lobster expressed in the recombinant baculovirus containing the untranslated region of 21 base pairs of the present invention was much higher than the expression level of tropomyosin of rabbit skeletal muscle expressed in the recombinant baculovirus not containing the untranslated region of 21 base pairs of the present invention. The density of the position corresponding to tropomyosin on acrylamide gel was 123 ODU on average (optical density unit) (n=3). The total amount of protein in 3L culture after the partial purification was about 0.8 to 1.5 g. The ratio of tropomyosin to total proteins was estimated by densitometry to be about 80%. Therefore, the amount of the expressed tropomyosin was evaluated to be about 0.6 to 1.2 g in 3L. Thus, it is confirmed that the ODU of the expression level and the expressed protein after partial purification of lobster tropomyosin expressed in the recombinant baculovirus containing the untranslated region of 21 base pairs of the present invention was about 10 times higher and more than 30 times higher than those for rabbit tropomyosin expressed in the recombinant baculovirus not containing the untranslated region of 21 base pairs of the present invention in Comparative Example 2, respectively.

Example 6

Expression of Rabbit Skeletal Muscle Tropomyosin Using Baculovirus Vector Containing the Untranslated Region of 21 Base Pairs from Lobster Tropomyosin Gene Rabbit tropomyosin was expressed and the expression level was determined as described above. The density of the position corresponding to tropomyosin on acrylamide gel was 107 ODU on average (n=3). Although these samples were not subjected to partial purification, about 9-fold expression of the protein was confirmed from comparison of ODU with those in Comparative Example not containing the untranslated region of 21 base pairs.

Comparative Example 2

Expression of Rabbit Skeletal Muscle Tropomyosin Using a Recombinant Baculovirus Vector not Containing the Untranslated Region of 21 Base Pairs of the Present Invention Rabbit tropomyosin was expressed and the expression level was determined as described above. The density of the position corresponding to tropomyosin on acrylamide gel was 12 ODU. on average. The total amount of the protein in a 3L culture after the partial purification was about 100 to 150 mg. The ratio of tropomyosin to total proteins was estimated by densitometry to be about 20%. Therefore, the amount of the expressed tropomyosin was estimated as about 20 to 30 mg in 3L.

Example 7

Construction of a Transfer Vector to Express a Mutant Luciferase from a Firefly

A 0.2 ml tube was charged with 50 picomole of pGL3-Basic Vector (Promega), each 50 pico mole of the following two synthetic DNAs, namely, ctgttggtaa agccaccatg g (SEQ ID NO:4) and ggatccttac acggcgatct ttccgc (SEQ ID NO:5), 1 µl of ExTaq polymerase (Takara), 5 µl of the 10xbuffer appended to the polymerase, and 4 µl of dNTP mixture and the final volume of the solution in the tube was adjusted to 50 µl with distilled water. Then, the tube was loaded on a PCR apparatus, Perkin-Elmer model 9700 to carry out PCR using a reaction program comprising 93° C. for 5 minute, 25 cycles comprising each cycle of 93° C. for 1 minute, 55° C. for 2 minutes and 72° C. for 1 minute, and 72° C. for 10 minutes. The PCR product contained a restriction enzyme NcoI site, the entire translated region, and a restriction enzyme BamHI site. Both the PCR product and the transfer vector, pAcC4 were digested with the restriction enzymes NcoI/BamHI (Takara) and then subjected to a 0.8% TAE-agarose gel electrophoresis. After the electrophoresis, the gel was stained with ethidium bromide and its DNA bands were detected on a transilluminator. The bands of the mutant luciferase DNA and pAcC4 fragments were cut by a cutter to extract the DNAs using a Gene Clean II Kit (BIO101). These DNAs were mixed, followed by addition of T4 DNA ligase (Takara) and a buffer appended to the ligase and the mixture was incubated at 16° C. for overnight. After the incubation, E. coli cells were transformed with the resulting base sequence and grown on an LB agar medium containing ampicillin to form colonies. The formed colonies were picked up with a toothpick and cultured on a Circle grow medium (BIO101) to be well grown. The transfer vector was prepared by using Plasmid Maxi Prep Kit (Qiagen). In the transfer vector, the mutant luciferase gene from a firefly is inserted downstream of the initiation codon of original polyhedrin downstream of polyhedrin promoter.

Example 8

Construction of a Transfer Vector to Express the Mutant Luciferase from a Firefly, Wherein Said Transfer Vector Comprises the Untranslated Region of 21 Base Pairs From Lobster Tropomyosin Gene The construction of the transfer vector to express the mutant luciferase from a firefly wherein the transfer vector contains the untranslated region of 21 base pairs from lobster tropomyosin was carried out in the similar manner to the construction of the transfer vector to express the mutant luciferase from a firefly mentioned above. The different point was that the mutant luciferase gene from a firefly was inserted not into the transfer vector pAcC4 but the transfer vector to express the lobster muscle tropomyosin digested with NcoI/BamHI to remove the translated region of lobster tropomyosin. In this transfer vector, the initiation codon of original polyhedrin downstream of polyhedrin promoter had been destroyed and the mutant luciferase gene from firefly is inserted into downstream of the untranslated region of 21 base pairs from lobster tropomyosin gene adjacent to XbaI site further downstream.

Preparation of the Recombinant Baculovirus and Amplification Thereof

Preparation of the recombinant baculovirus and its amplification were carried out in the same manner as those in Example 3. Plaque assay and amplification of the baculovirus were also carried out in the same manner as in Example 3.

Expression of the Mutant Luciferase From a Firefly

Sf9 cells ($7.5 \times 10^6$/10 ml) were fixed on a dish surface. The cells were infected with the virus prepared in <Amplification of the virusIII> with moi of 2 and incubated at 27° C. for 2 hours. After that, the medium was removed from the dish and a fresh modified Sf9 OOII medium was added to it and the dish was incubated at 27° C. for 48 hours. The cells were removed from the dish, put into a 15 ml centrifuge tube (Falcon) and centrifuged at 1,200×G for 10 minutes. The supernatant was discarded. The collected cells were suspended in 500 µl of a hypotonic cell-lysing solution II (20 mM Tris HCl, pH 8.0, 5 mM 2-mercaptoethanol) and the cells were destroyed by pipetting. The lysate was transferred to a 1.5 ml tube and the tube was centrifuged on a centrifuge (Tomy, model MX-160) at 15,000 rpm for 15 minutes. The supernatant was collected and diluted 1000 times with the hypotonic cell-lysing solution II described above. Twenty µl of the diluted solution was added to a luminometer cuvette and mixed with 100 µl of a Luciferase Assay Reagent (Promega) using a autoinjecter and determined the luminescence. The integrated luminescence between 8 and 18 seconds after the mixing was defined as RLU.

In results, in the case of recombinant baculovirus containing the leader sequence of the present invention, 15208.4RLU(n=5). were observed as compared with 2162.0RLU (n=5) in the case of not containing the leader sequence of the present invention. The ratio of the former to the latter was about 7.

Effect of the Invention

It is possible to remarkably enhance the expression level of a polypeptide of interest by ligating the coding sequence encoding the polypeptide of interest downstream of the polynucleotide sequence of the present invention (as set forth in SEQ ID NO:1) or a part thereof or a polynucleotide sequence containing the sequence of the present invention or a part thereof. Also, it is possible to easily produce the polypeptide of interest in large amount by expression of the polypeptide in the living cells using the transfer vector of the present invention or the recombinant baculovirus of the present invention.

What is claimed is:

1. An isolated nucleic acid consisting essentially of the nucleotide sequence of SEQ ID NO. 1 wherein said nucleic acid enhances expression of a polypeptide coding sequence located downstream thereof.

2. A transfer vector comprising the isolated nucleic acid of claim 1.

3. A recombinant baculovirus comprising the nucleic acid of claim 1.

4. The transfer vector of claim 2 further comprising a DNA sequence encoding a polypeptide of interest downstream of the isolated nucleic acid.

5. The transfer vector of claim 4 wherein said isolated nucleic acid and said DNA sequence encoding a polypeptide of interest are located downstream of a promoter sequence from baculovirus.

6. The transfer vector of claim 5 wherein said promoter sequence from baculovirus is a polyhedrin promoter sequence.

7. The recombinant baculovirus of claim 3 wherein the nucleic acid is integrated into said baculovirus by in vivo homologous recombination.

8. The recombinant baculovirus of claim 3 wherein the nucleic acid is integrated into said baculovirus by means of a transposable element.

9. The recombinant baculovirus of claim 7 wherein said homologous recombination occurs in an insect or a cultured insect cell capable of being a host for baculovirus.

10. The recombinant baculovirus of claim 7 wherein said homologous recombination occurs in an *E. coil* cell.

11. The recombinant baculovirus of claim 7 wherein said homologous recombination occurs in a yeast cell.

12. The recombinant baculovirus of claim 9 wherein said insect is a silkworm.

13. The recombinant baculovirus of claim 9 wherein said cultured insect cell is an Sf8, Sf21 or a cell derived from Trichoplusia ni.

14. An isolated nucleic acid consisting essentially of a nucleic acid obtained by deletion, substitution, insertion and/or addition of one or more of the nucleotides of SEQ ID NO:1 and wherein said nucleic acid enhances expression of a polypeptide coding sequence located downstream thereof.

15. A method for producing a polypeptide of interest comprising:
   infecting an insect or a cultured insect cell with the recombinant baculovirus of claim 3;
   maintaining said insect or said cultured insect cell under conditions wherein said polypeptide is expressed; and
   collecting the expressed polypeptide of interest.

16. The method of claim 15 wherein said insect is silkworm.

17. The method of claim 15 wherein said cultured insect cell is an Sf9, Sf21 or a cell derived from Trichoplusia ni.

18. A method for producing a polypeptide of interest comprising:
   (a) generating a recombinant baculovirus comprising the nucleotide sequence of SEQ ID NO. 1, and the coding sequence for a polypeptide of interest, the expression of which is desired;
   (b) infecting an insect or a cultured insect cell with the recombinant baculovirus; and
   (c) maintaining said insect or said cultured insect cell under conditions wherein said polypeptide of interest is expressed.

19. The method of claim 18 wherein step (a) is preceded by the step of preparing a transfer vector comprising the nucleotide sequence of SEQ ID NO. 1 and the coding sequence for a polypeptide of interest.

20. The method of claim 18 wherein step (c) is followed by (d) collecting the expressed polypeptide of interest.

21. The method of claim 18 wherein said recombinant baculovirus is generated by in vivo homologous recombination of a transfer vector containing said nucleotide sequence of SEQ ID NO. 1 and the coding sequence of the polypeptide of interest with said baculovirus or by transposition of said nucleotide sequence of SEQ ID NO. 1 and said coding sequence into said baculovirus by means of a transposable element.

22. An isolated nucleic acid comprising:
   a) a translation enhancing element comprising the nucleotide sequence of SEQ ID NO:1; and
   b) a nucleotide sequence encoding a polypeptide, other than lobster tropomyosin, the expression of which is desired wherein said nucleotide sequence is operably linked downstream of said translation enhancing element.

23. A transfer vector comprising the isolated nucleic acid of claim 22.

24. A recombinant baculovirus comprising the nucleic acid of claim 22.

25. The transfer vector of claim 23 wherein said isolated nucleic acid is located downstream of a promoter sequence from baculovirus.

26. The transfer vector of claim 25 wherein said promoter sequence from baculovirus is a polyhedrin promoter sequence.

27. The recombinant baculovirus of claim 24 wherein the isolated nucleic acid of claim 26 is integrated into said baculovirus by in vivo homologous recombination.

28. The recombinant baculovirus of claim 24 wherein an isolated nucleic acid consisting essentially of SEQ ID NO:1 is integrated into said baculovirus by means of a transposable element.

29. A method for producing a polypeptide of interest comprising:
   infecting an insect or a cultured insect cell with the recombinant baculovirus of claim 24;
   maintaining said insect or said cultured insect cell under conditions wherein said polypeptide is expressed; and
   collecting the expressed polypeptide of interest.

30. The recombinant baculovirus of claim 27 wherein said homologous recombination occurs in an insect or a cultured insect cell capable of being a host for baculovirus.

31. The recombinant baculovirus of claim 27 wherein said homologous recombination occurs in a yeast cell.

32. The recombinant baculovirus of claim 27 wherein said homologous recombination occurs in an *E. coli* cell.

33. The recombinant baculovirus of claim 30 wherein said insect is a silkworm.

34. The recombinant baculovirus of claim 30 wherein said cultured insect cell is an Sf8, Sf21 or a cell derived from Trichoplusia ni.

35. The method of claim 29 wherein said insect is silkworm.

36. The method of claim 29 wherein said cultured insect cell is an Sf9, Sf21 or a cell derived from Trichoplusia ni.

37. An isolated nucleic acid comprising:
   a) a translation enhancing element comprising a nucleotide sequence obtained by deletion, substitution, insertion and/or addition of one or more of the nucleotides of SEQ ID NO:1 and
   b) a nucleotide sequence encoding a polypeptide, other than lobster tropomyosin, the expression of which is desired wherein said nucleotide sequence is operably linked downstream of said translation enhancing element.

* * * * *